United States Patent [19]

Sterzer

[11] Patent Number: 4,924,863

[45] Date of Patent: May 15, 1990

[54] ANGIOPLASTIC METHOD FOR REMOVING PLAQUE FROM A VAS

[75] Inventor: Fred Sterzer, Lawrence Township, Mercer County, N.J.

[73] Assignee: MMTC, Inc., Princeton, N.J.

[21] Appl. No.: 190,179

[22] Filed: May 4, 1988

[51] Int. Cl.⁵ ............................................. A61B 17/36
[52] U.S. Cl. ................................................... 606/27
[58] Field of Search ...................... 128/303.1, 395–398; 604/96, 101, 102

[56] References Cited

U.S. PATENT DOCUMENTS

| | | | |
|---|---|---|---|
| 3,858,577 | 1/1975 | Bass et al. ............................ | 128/398 |
| 4,641,649 | 2/1987 | Walinsky et al. ................. | 128/303.1 |
| 4,643,186 | 2/1987 | Rosen et al. ...................... | 128/303.1 |
| 4,747,405 | 5/1988 | Leckrone ........................... | 128/303.1 |
| 4,808,164 | 2/1989 | Hess ................................... | 128/303.1 |

Primary Examiner—Max Hindenburg
Attorney, Agent, or Firm—George Seligsohn

[57] ABSTRACT

Fatty artherosclerotic plaque, under heat (e.g. by applied microwave radiation) and pressure, is liquified and sucked into the interior of one of two catheters of a catheter arrangement through an aperture therein and then sucked out of a patient's body through the proximal end of the one catheter. The other of the two catheters employs an inflated balloon to press the aperture region of the one catheter firmly against the plaque portion to be removed. Calcified artherosclerotic plaque can be ablated and removed in a similar manner, by substituting ultrasonic energy for heat.

8 Claims, 2 Drawing Sheets

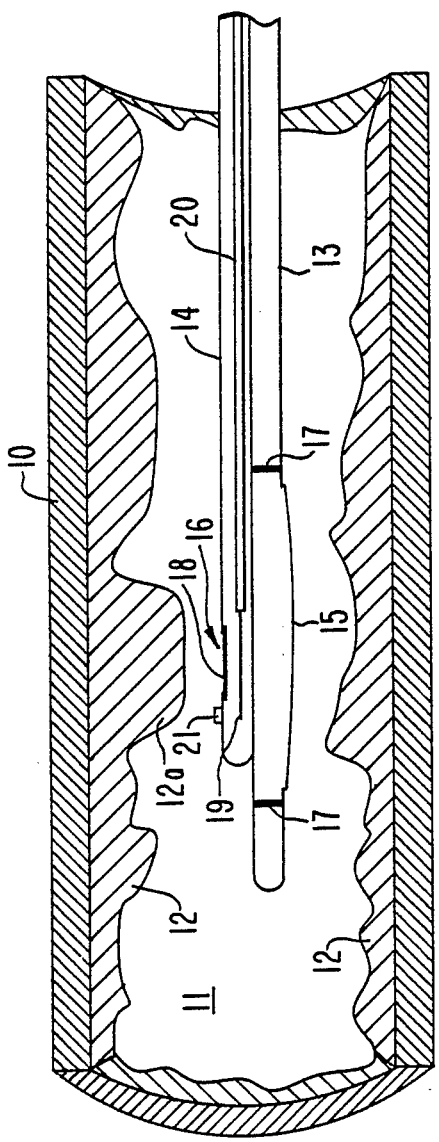
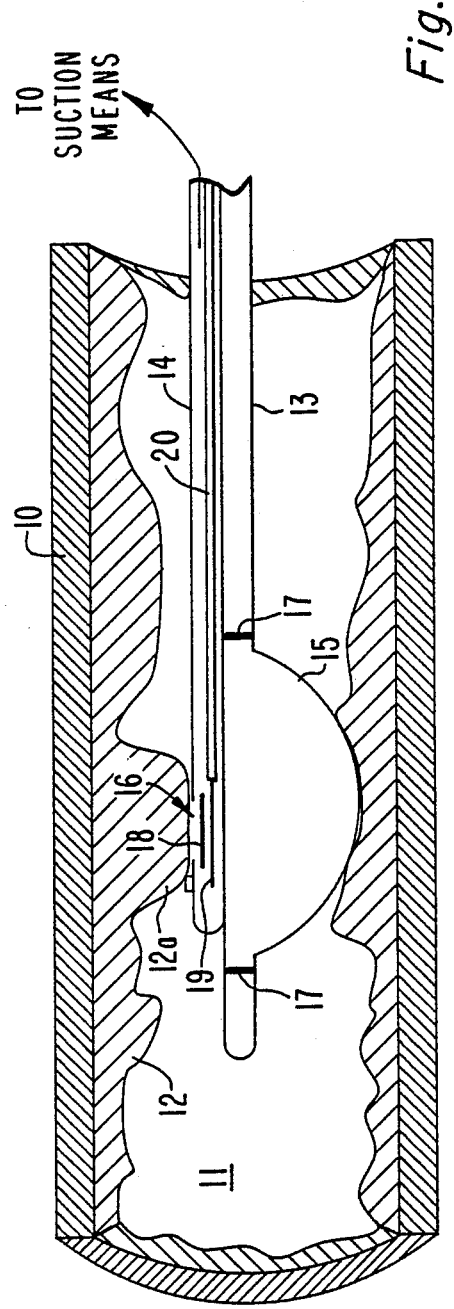

ANGIOPLASTIC METHOD FOR REMOVING PLAQUE FROM A VAS

BACKGROUND OF THE INVENTION

1. Field of the Invention

This invention relates to an improvement in percutaneous transluminal angioplasty, which improvement permits the removal of plaque material from a vas.

2. Description of the Prior Art

It is known that artherosclerotic plaque tends to form in a vas, such as an artery, of a large number of people. Such plaque on the wall of a vas, which partially occludes the lumen or channel of the vas, may occur in coronary blood vessels or in peripheral blood vessels. In the case of coronary blood vessels, the reduced blood flow caused thereby results in chronic heart problems, including miocardial infarction. The narrowing of the lumen of peripheral blood vessels, such as an artery of the leg, by the partial occlusion thereof by artherosclerotic plaque is also a recognized problem.

One of several known treatments for the partial occlusion of the lumen of a vas by artherosclerotic plaque, is percutaneous transluminal balloon catheter angioplasty. This method involves insertion of a deflated balloon into the lumen of an artery that is partially obstructed by plaque, and then inflating the balloon in order to enlarge the lumen by means of pressure exerted by the inflated balloon on the plaque. More specifically, the initial existence of protuberance of plaque in a vas acts as a bottleneck that severly restricts the flow of blood. The plaque protuberence is squeezed by the balloon, thereby causing deformation and smoothing of the shape of the plaque surface that substantially eliminates the protuberance, thus enlarging the lumen. In order to make the plaque deform more easily, the plaque may be softened somewhat by heat applied thereto. In this regard, reference is made to U.S. Pat. No. 4,643,186, which issued to Rosen et al. on Feb. 17, 1987, and is entitled "Percutaneous Transluminal Microwave Catheter Angioplasty" This patent discloses the use of radio-frequency or microwave frequency electrical energy radiated from an antenna within the interior of a balloon catheter into a plaque protuberence to heat and soften the plaque material so that the plaque material is more easily deformed and smoothed by the pressure exerted by the balloon portion of the catheter.

Regardless of whether or not the plaque material is softened by heat, a mere deformation in the shape of the plaque material, within the vas, and not in the removal from the vas of any of the mass of the plaque material, results in the bore of the treated vas being narrower than it would be if, in addition to the smoothing of the surface of the plaque, at least a portion of the mass of the plaque material were removed from the vas.

Although somewhat dangerous, it becomes necessary at times, in performing percutaneous transluminal balloon catheter angioplasty as is presently practiced, to apply sufficient pressure on the wall of a vas, such as an artery to break the surrounding arterial muscle in order to achieve a significant widening of the lumen of the artery.

Another technique which has recently received a good deal of attention is transluminal laser catheter angioplasty. This treatment involves introduction into the coronary artery of a fiber optic cable the proximal end of which is connected to a laser energy source. The distal end of the fiber optic cable is directed towards the plaque. The laser is pulsed, and the resulting high energy light pulse vaporizes a portion of the plaque. Many problems remain unsolved in laser catheter angioplasty. Locating the plaque requires some means such as a fiber optic scope to see the region towards which the laser pulse will be directed. The interior of the artery must be illuminated, and a clear liquid introduced into the artery to displace opaque blood from the region to be viewed. Even with a fiber optic scope, however, the plaque may be difficult to distinguish from normal arterial walls. When the energy of the laser discharge is directed towards the arterial walls, the walls may undesirably be perforated. Further problems related to the difficulty in matching the characteristic of lasers and fiber optic cables to the frequency absorption characteristics of various types of plaque, and the by-products of the destruction of the plaque.

The present invention makes it possible to use percutaneous transluminal balloon catheter angioplasty to more safely remove plaque material from the vas than is the case with transluminal laser catheter angioplasty.

SUMMARY OF THE INVENTION

The present invention is based in part on the discovery that when fatty arthrosclerotic plaque under pressure is heated to a relatively high temperature (e.g. 44° C.) for a limited time (e.g. for 10 minutes more or less), at least a portion of the fatty artheroslerotic plaque liquifies and rises to the surface of the plaque without causing death of underlying tissue. Furthermore, calcified artherosclerotic plaque can be ablated from the surface thereof by the use of ultrasonic energy, rather than heat energy.

More generally, the present invention is directed to an angioplastic method for removing at least a portion of plaque initially in non-removable form that partially occludes the lumen of a vas, thereby to increase the size of the lumen. A first step the method of the present invention is the insertion into the vas of a catheter arrangement having (1) a deflated balloon, and (2) an aperture. The deflated balloon is disposed off-center of a longitudinal axis of the catheter arrangement in a first sidewall of the catheter arrangement, and the deflated balloon is located at a given longitudinal position situated toward the distal end of the catheter arrangement. The aperture is also disposed off-center of the longitudinal axis of the catheter arrangement in a second sidewall of the catheter arrangement that is located substantially opposite the first sidewall, and the aperture is located substantially at the given longitudinal position. The catheter arrangement further includes (3) means for preventing gas within the catheter arrangement from entering the vas through the aperture while the balloon is deflated.

A second step of the angioplastic method of the present invention is to position the catheter arrangement so that the aperture is in proximity to the plaque that includes the portion to be removed.

A third step is to inflate the balloon so that the balloon presses against a part of a wall of the vas located substantially opposite to the plaque which includes the portion to be removed. This causes the aperture to be pressed against the plaque that includes the portion to be removed with sufficient firmness to prevent any fluid in the vas from entering the interior of the catheter arrangement while the balloon is inflated.

A fourth step is, while the balloon is inflated, to apply energy of a predetermined type to the plaque which includes the portion to be removed. This energy of the predetermined type causes the portion of the plaque to be removed to be converted from a non-removable form to a removable form without death of underlying tissue of the vas.

A fifth step is, while the balloon is inflated, to apply sufficient suction to the interior of the catheter arrangement to reduce the relative pressure within the interior of the catheter arrangement in the vicinity of the aperture by an amount which causes the plaque portion in removable form being sucked into the interior of the catheter arrangement through the aperture and then being sucked out of the catheter arrangement at the proximal end thereof.

The present invention is also directed to apparatus comprising the structure of the aforesaid catheter arrangement.

BRIEF DESCRIPTION OF THE DRAWING

In the Drawing:

FIG. 1a is a diagramatic illustration of a first embodiment of the catheter arrangement of the present invention, in which the balloon portion thereof is deflated;

FIG. 1b is a diagramatic illustration of the first embodiment of the present invention, in which the balloon portion thereof is inflated;

DESCRIPTION OF THE PREFERRED EMBODIMENTS

Figure 2A:
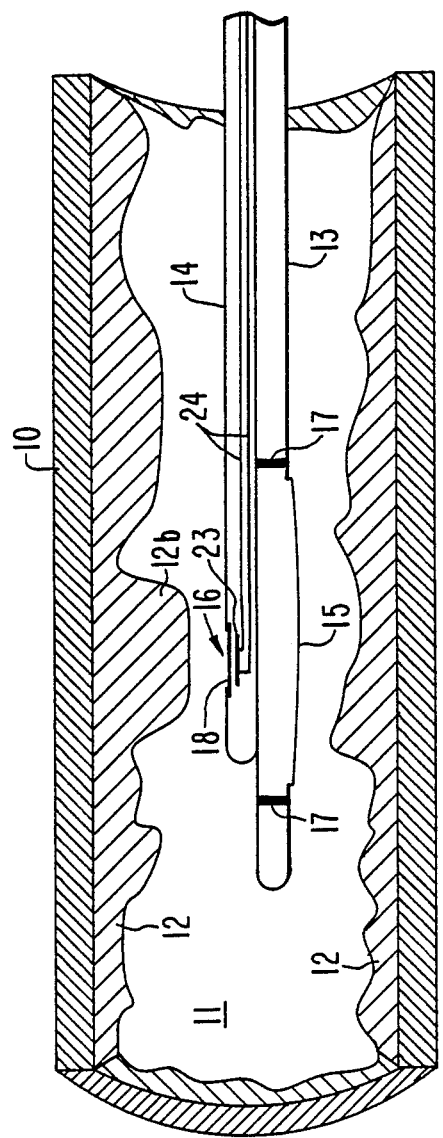
FIG. 2a is a diagramatic showing of a second embodiment of the present invention, in which the balloon portion thereof is deflated.

Referring to FIG. 1, there is shown a portion of the length of a vas, such as a coronary artery. The lumen 11 of vas 10 is partially occluded by the presence of artherosclerotic plaque 12 attached to the wall of vas 10. Plaque 12 includes plaque portion 12a to be operated on for the purpose of removing some of the mass of plaque portion 12a.

Inserted in lumen 11 of vas 10 is the more distal region of a catheter arrangement comprised of first and second juxtaposed catheters 13 and 14, respectively, which are attached to one another along a longitudinal axis. First catheter 13 includes a balloon portion 15 located at a given longitudinal position situated toward the distal end of first catheter 13. In FIG. 1, balloon portion 15, which is disposed off-center of the longitudinal axis of the catheter arrangement in the sidewall of catheter 13, is shown deflated.

Second catheter 14 includes aperture 16 in an outer sidewall therof with respect to the longitudinal axis. Aperture 16 is located substantially at the same given longitudinal position. Therefore, balloon portion 15 of first catheter 13 and aperture 16 of second catheter 14 are situated substantially diametrically opposite to one another.

As is known in angioplasty, the distal end of a catheter is inserted into the vascular system of the patient from outside the patient's body and then is pushed through the patient's vascular system until the balloon portion toward the distal end thereof is properly positioned with respect to the plaque portion to be operated on. Thus, the proximal end of the angioplastic catheter arrangement is situated outside the patient's body.

With balloon portion 15 deflated, as shown in FIG. 1, the catheter arrangement can be easily moved through the vascular system of the patient. However, the exact position of balloon portion 15 must be known to the operator of the catheter arrangement in order to properly position balloon portion 15 with respect to the piece of plaque portion 12a to be operated upon. In order to accomplish this, radio-opaque rings 17 define the longitudinal interval of catheter 13 occupied by balloon portion 15. This enables the operator to employ fluoroscopic techniques, known in the art, to accurately position balloon portion 15 and, hence, aperture 16 with respect to plaque portion 12a to be operated on.

While the catheter arrangement is being inserted, with balloon portion 15 in its deflated state, it becomes necessary to prevent gas (e.g. air) present in the interior of second catheter 14 from entering the blood that is flowing in lumen 11 through aperture 16. In order to accomplish this, normally-closed check-valve 18 maintains aperture 16 closed while balloon portion 15 is in its deflated state.

Situated as shown in proximity to aperture 16, within the interior of second catheter 14, is antenna 19 capable of radiating microwave or radio-frequency energy when energized by microwave or radio-frequency energy applied thereto over a flexible transmission line 20 (e.g. coaxial cable) that extends to the proximal end of second catheter 14 situated outside of the patient's body. However, it should be understood that no microwave or radio-frequency energy is normally applied through transmission line 20 to antenna 19 while the catheter arrangement is being properly positioned with respect to plaque portion 12a to be operated on, with balloon portion 15 in its deflated state.

Attached to the outside of second catheter 14, immediately next to aperture 16, is small thermistor 21. Wires (not shown) coupled to thermistor 21 through the sidewall of second catheter 14, extend through the length of second catheter 14 to the proximal end thereof outside the patient's body.

Only after the catheter arrangement, with balloon portion 15 in its deflated state, has been properly positioned with respect to the plaque portion 12a to be operated on, is balloon portion 15 of first catheter 13 inflated by filling the interior of catheter 13 with a liquid (which maybe radio-opaque). More specifically, as shown in FIG. 1b balloon portion 15, while inflated, presses against a part of a wall of vas 10 located substantially opposite plaque portion 12a to be operated on. This causes aperture 16 to be pressed against plaque portion 12a to be operated on with sufficient firmness to prevent any fluid (e.g. blood) flowing through lumen 11 of vas 10 from entering interior of catheter 14 through aperture 16. Furthermore, thermistor 21 is placed in intimate contact with portion of plaque portion 12a to be operated on.

While balloon portion 15 is inflated, antenna 19 is energized through transmission line 20, thereby radiating microwave or radio-frequency energy into plaque portion 12a to be operated on. The microwave or radio-frequency energy radiated into plaque portion 12a dielectrically heats plaque portion 12a for a limited time to a relatively high temperature (e.g. 44° C.) at which at least of portion of fatty material comprising plaque portion 12a being operated on becomes liquified, but which temperature and time are still safe for the tissue of vas 10 underlying plaque portion 12a. Thermistor 21 is employed to sense the temperature of plaque portion 12a so that the amount of microwave or radio-frequency energy applied to antenna 19 can be controlled (by means not shown) to prevent overheating that might damage the tissue of vas 10 underlying plaque portion 12a. Because at this time, with balloon portion 15, inflated plaque portion 12a is under pressure by second catheter 14 in contact therewith, the liquified fatty material rises to the surface of plaque portion 12a that is in contact with aperture 16.

Further, while balloon portion 15 is inflated, suction is applied to the interior of second catheter 14 by suction means (not shown) coupled to the proximal end second catheter 14 outside the patient's body. Presence of this suction causes liquified fatty material that has risen to the surface of plaque portion 12a in contact with aperture 16 to be sucked into the interior of catheter 14 through aperture 16, and then sucked through second catheter 14 and then out of the patient's body through the proximal end of second catheter 14. Any tendency for the liquified fatty material to resolidify while being sucked out of second catheter 14, can be avoided by suitably heating the interior of the length of second catheter 14. This can be accomplished by resistance heating wires located (1) within the wall of second catheter 14, (2) within the sheath of transmission line 20, (3) separately within the interior of second catheter 14, or (4) any combination of the above. In this manner, the mass of plaque portion 12a is reduced by the removal of least some of the fatty material of plaque portion 12a from the patient's body. In addition, the heat and pressure applied to plaque portion 12a results in the deformation and the smoothing of the remainder of plaque portion 12a, as known in the prior art.

After the removal of the liquified fatty material from plaque portion 12a has been completed, balloon portion 15 of first catheter 13 is deflated, by letting liquid therein escape, and then the catheter arrangement is removed from the patient's body.

As is known, besides there being fatty artherosclerotic plaque, there is also calcified artherosclerotic plaque. The embodiment of the present invention shown in FIGS. 2a and 2b may be employed to remove calcified artherosclerotic plaque from a vas of a patient.

Figure 2B:
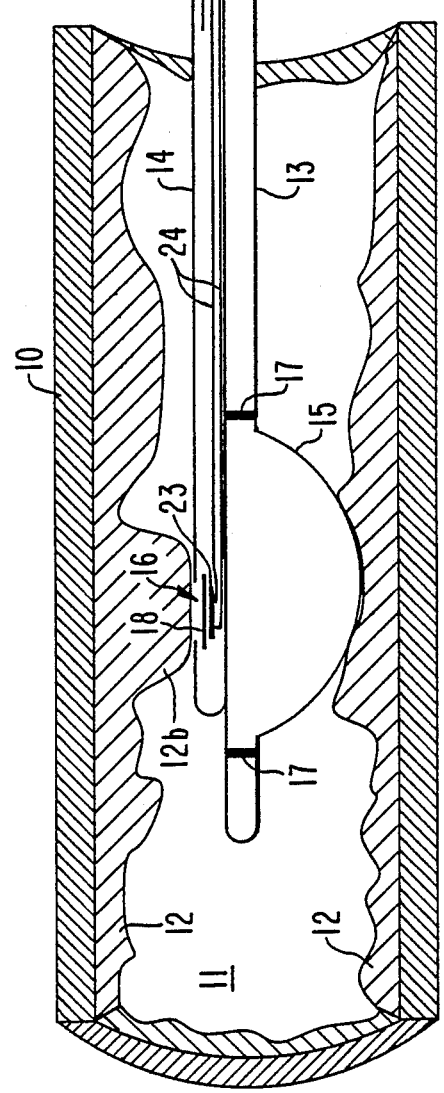
FIG. 2b is a diagramatic illustration of the second embodiment of the present invention, in which the balloon portion thereof is inflated.

Specifically, calcified artherosclerotic plaque portion 12b shown in FIGS. 2a and 2b, is radiated with ultrasonic energy to convert the calcified material on the surface of artherosclerotic plaque portion 12b from a non-removable form to a removable form by ablation. More particularly, the catheter arrangement shown in FIGS. 2a and 2b is similar to the catheter arrangement shown in FIGS. 1a and 1b except for the fact that antenna 19 in FIGS. 1a and 1b is replaced by ultrasonic transducer 23 in FIGS. 2a and 2b and transmission line 20 coupled to antenna 19 in FIGS. 1a and 1b is replaced in FIGS. 2a and 2b by transmission line 24 coupled to ultrasonic transducer 24 transmission line 24 applies electrical energy at an ultrasonic frequency as an input to ultrasonic transducer 23.

In operation, the applied ultrasonic energy is ablates material from the surface of calcified artherosclerotic plaque 13b while the balloon portion 15 is inflated and aperture 16 is pressed against plaque portion 12b. The ablated calcified artherosclerotic material from plaque portion 12b is removed from the patient's body by suction applied to the proximal end of second catheter 14.

Certain modifications may be made in the structure of the catheter arrangements shown in FIGS. 1a, 1b, 2a and 2b, and described above in detail without departing from the principles of the present invention. For instance, in the case of the first embodiment of the first invention as shown in FIGS. 1a and 1b, heat may be applied to fatty artherosclerotic plaque portion 12a by other means than by radiated microwave or radio-frequency energy. For example, a resistance element heated by DC current can be substituted for antenna 19 in the vicinity of aperture 16. Furthermore, in the case of a peripheral artery situated close to the skin of a patient, such as an artery in the leg, it is possible to dielectrically heat fatty artherosclerotic plaque portion 12a with microwave or radio-frequency energy radiated thereto through the skin from outside the patient's body. In this latter case, both antenna 19 and transmission line 20 may be omitted from second catheter 14 of the catheter arrangement. However, in all cases, the plaque material in removable form, whether liquified or ablated from the plaque portion being operated on, is removed from the body by being sucked through the aperture and then through the interior of the catheter arrangement to outside the patient's body, while the balloon portion of the catheter arrangement is inflated and the aperture is pressed against the plaque portion being operated on.

In the embodiments shown in FIGS. 1a, 1b, 2a and 2b, normally-closed check-valve 18 is employed for preventing gas from entering lumen 11 of vas 10 through aperture 16 when balloon portion 15 is deflated. However, this is not the only way for preventing gas from entering lumen 11 of vas 10. For instance, valve 18 can be omitted and, in its place suction can be applied to the interior of second catheter 14 while balloon portion 15 is deflated (i.e., while the inserted catheter arrangement is being positioned with respect to either plaque portion 12a or 12b. In this case, the reduced pressure within the interior of second catheter 14 causes blood in lumen 11 to be sucked into the interior of second catheter 14 through aperture 16 while balloon portion 15 is deflated, thereby preventing any gas from escaping from second catheter 14 into the bloodstream flowing in lumen 11. When balloon portion 15 is inflated, aperture 16 is pressed against the plaque with sufficient firmness to prevent any fluid in vas 10 from entering the interior of second catheter 14. Therefore, any residual blood still in the interior of second catheter 14 at this time will be all sucked out of the patient through the proximal end of second catheter 14. Thereafter, the removable material from plaque portion 12a or 12b liquid or ablated material, as the case may be, is sucked through aperture 16 and the length of second catheter 14 in the manner described above.

What is claimed is:

1. A transluminal balloon angioplastic method for removing at least a portion of fatty artherosclerotic plaque initially in non-removable form that partially occludes the lumen of a vas, thereby to increase the size of the lumen; said method comprising the steps of:
   (a) inserting into said vas a catheter arrangement having:
      (1) a deflated balloon disposed off-center of the longitudinal axis of said catheter arrangement in a first sidewall of said catheter arrangement, said deflated balloon being located at a given longitudinal position situated toward the distal end of said catheter arrangement;

(2) an aperture disposed off-center of the longitudinal axis of said catheter arrangement in a second sidewall of said catheter arrangement that is located substantially opposite to said first sidewall, said aperture being located substantially at said given longitudinal position; and (3) means for preventing gas from entering said vas through said aperture while said balloon is deflated;

(b) positioning said catheter arrangement so that said aperture is in proximity to the fatty artherosclerotic plaque which includes said portion to be removed;

(c) inflating said balloon so that said balloon presses against a part of a wall of said vas located substantially opposite to the fatty artherosclerotic plaque which includes said portion to be removed, thereby causing said aperture to be pressed against the fatty artherosclerotic plaque that includes said portion to be removed with a first pressure that provides sufficient firmness to prevent any fluid in said vas from entering the interior of said catheter arrangement through said aperture while said balloon is inflated;

(d) while said balloon is inflated, applying heat energy for a limited time to the fatty artherosclerotic plaque which includes said portion to be removed, which applied heat energy raises the temperature of the fatty artherosclerotic plaque under said first pressure to a value which is sufficient to cause at least a portion thereof to liquify and rise to the surface of the plaque then in contact with said aperture, but which temperature is insufficient to cause death of underlying tissue of said vas; and (e) while said balloon is inflated, applying sufficient suction to the interior of said catheter arrangement to reduce the relative pressure within the interior of said catheter arrangement in the vicinity of said aperture to a second pressure to cause said liquified plaque portion being sucked into the interior of said catheter arrangement through said aperture and then being sucked out of said catheter arrangement at the proximal end thereof.

2. The angioplastic method defined in claim 1, further including the following step:

(f) subsequent to the completion of steps (d) and (e), deflating said balloon and then removing said catheter arrangement from said vas.

3. The angioplastic method defined in claim 2, further including the following step:

(g) subsequent to the completion of steps (d) and (e), terminating the application of said heat energy.

4. The angioplastic method defined in claim 1, wherein:

step (a) comprises inserting into said vas a catheter arrangement comprised of first and second juxtaposed catheters attached to one another along said longitudinal axis, only said first catheter including said balloon and only said second catheter including said aperture, said balloon and said aperture being situated substantially diametrically opposite to one another;

step (c) comprises filling solely the interior of said first catheter with a liquid to inflate said balloon; and step (e) comprises applying suction soley to the interior of said second catheter.

5. The angioplastic method defined in claim 1, wherein:

said heat energy defined in step (d) is dielectrically generated within said fatty artherosclerotic plaque by microwave or radio frequency energy applied thereto.

6. The angioplastic method defined in claim 5; wherein:

step (a) comprises inserting into said vas a catheter arrangement comprised of first and second juxtaposed catheters attached to one another along said longitudinal axis, only said first catheter including said balloon and only said second catheter including said aperture, and said second catheter also including in the interior thereof (1) an antenna situated in proximity to said aperture for raidating microwave or radio-frequency energy into said fatty artherosclerotic plaque and (2) a transmission line coupled to said antenna and extending to the proximate end of said second catheter for applying microwave or radio-frequency energy to said antenna.

7. The angioplastic method defined in claim 1, wherein:

said predetermined type of energy defined in step (d) is ultrasonic energy in a sufficient amount to cause calcified artherosclerotic plaque material to be ablated at the surface thereof in contact with said aperture when said aperture is pressed against the plaque as defined in step (c), said ablated calcified artherosclerotic material constituting plaque in a removable form.

8. The angioplastic method defined in claim 7, wherein:

step (a) comprises inserting into said vas a catheter arrangement comprised of first and second juxtaposed catheters attached to one another along said longitudinal axis, only said first catheter including said balloon and only said second catheter including said aperture, and said second catheter also including in the interior thereof (1) an ultrasonic transducer in proximity to said aperture for radiating ultrasonic energy onto said calcified artherosclerotic plaque, and (2) a transmission line coupled to said ultrasonic transducer and extending to the proximate end of said second catheter for applying ultrasonic-frequency electrical energy to said ultrasonic transducer.

* * * * *